United States Patent [19]

Gaffar et al.

[11] 4,348,381

[45] Sep. 7, 1982

[54] DENTAL REMINERALIZATION COMPOSITION

[75] Inventors: Abdul Gaffar, Somerset; Calvin B. Davis, North Brunswick, both of N.J.

[73] Assignee: Colgate-Palmolive Company, New York, N.Y.

[21] Appl. No.: 260,951

[22] Filed: May 6, 1981

[51] Int. Cl.$^3$ .......................... A61K 7/16; A61K 7/18
[52] U.S. Cl. ......................................... 424/52; 424/49; 424/57
[58] Field of Search ..................... 424/49-58

[56] References Cited

U.S. PATENT DOCUMENTS

| | | | |
|---|---|---|---|
| 3,886,204 | 5/1975 | Geffers et al. | 260/502.4 R |
| 3,886,205 | 5/1975 | Geffers et al. | 260/502.4 R |
| 4,080,440 | 3/1978 | DiGiucio et al. | 424/49 |
| 4,083,955 | 4/1978 | Grabenstetter et al. | 424/49 |
| 4,118,474 | 10/1978 | Gaffar et al. | 424/54 |
| 4,118,476 | 10/1978 | Gaffar et al. | 424/54 |
| 4,177,258 | 12/1979 | Gaffar et al. | 424/52 |
| 4,183,915 | 1/1980 | Gaffar et al. | 424/52 |
| 4,215,105 | 7/1980 | Gaffar et al. | 424/52 X |
| 4,224,308 | 9/1980 | Gaffar et al. | 424/49 |
| 4,224,309 | 9/1980 | Gaffar et al. | 424/54 |

*Primary Examiner*—Shep K. Rose
*Attorney, Agent, or Firm*—Robert L. Stone; Murray M. Grill; Herbert S. Sylvester

[57] ABSTRACT

An aqueous composition useful for remineralizing subsurface carious lesion, of dental enamel which comprises an aqueous solution which contains sources of calcium ions and phosphate ions as well as fluoride ions and further includes as an antinucleating agent, to stabilize the solution against precipitation, 2-phosphono-butane-tricarboxylic acid-1,2,4 or water soluble salt thereof, the pH of the solution being about 5-9, preferably close to physiological conditions, such as about 6.8-7.5.

16 Claims, No Drawings

DENTAL REMINERALIZATION COMPOSITION

This invention relates to a stable aqueous composition which is effective to remineralize carious lesions in dental enamel.

It is known that dental caries begin with lesions of so-call "white spots," which are demineralized areas below the surface of intact dental enamel. If unchecked, surface enamel above a sub-surface lesion eventually collapses, leading to cavitation and subsequent loss of tooth structure.

In order to arrest demineralization, and, indeed, in order to remineralize "white spots" various compositions have been proposed. For instance, U.S. Pat. No. 3,679,360 to Rubin et al discloses deposition of calcium phosphate from a gel onto a tooth surface. This, however, does not reach the sub-surface area where demineralization initially occurs. Further, because of the difficulty of maintaining both calcium ions and phosphate ions available without precipitating a calcium phosphate material, two part kits have been proposed in which a calcium component and a phosphate component are sequentially applied to the oral cavity as in British Pat. No. 1,408,922 to Raff et al, British Pat. No. 1,452,125 to Grabenstetter et al and U.S. Pat. No. 4,048,300 to Tomlinson et al, or mixed together shortly before such application to form a metastable system with temporary stability as in U.S. Pat. No. 4,080,440 to DiGiulio et al and British Pat. No. 1,509,977 to Levine. Another metastable solution has been described in U.S. Pat. No. 4,097,588 to Levine. Even this solution, however, is not substantially permanent and precipitation can occur, particularly when fluoride ions are present. British Pat. No. 1,468,149 to Levine is to similar effect. In British Pat. No. 1,516,505 to DiGiulio water is avoided and an anhydrous composition is used for remineralization.

It is an advantage of this invention that a one-part stable aqueous remineralizing composition is suitably prepared as a dental mouthrinse and also can be incorporated into other dentifrice compositions such as a dental cream or gel, mouth spray, troche, chewable tablet, lozenge and the like. Such compositions contain 2-phosphono-butane-tricarboxylic acid-1,2,4 or water-soluble salt thereof.

Further advantages will be apparent from consideration of the following specification.

In accordance with certain of its aspects, this invention relates to a stable aqueous remineralizing composition which comprises a solution of water having dissolved therein a source of calcium ions and a source of phosphate ions, the amount of calcium ion and phosphate ions being sufficient to effect remineralization of dental enamel; a compound which provides fluoride anticaries agent; and an antinucleating agent selected from the group consisting of 2-phosphono-butane-tricarboxylic acid-1,2,4 and water-soluble salt thereof, said solution having a pH about 5 to 9.

The antinucleating properties of the agents employed in the present invention appear to be effective to prevent precipitate from the calcium and phosphate ions in the dentifrice particularly with the fluoride ions also present. As described in Ciba Foundation Symposium, "Hard Tissue Growth Repair and Remineralization (Elsevier)," Associated Scientific Publishers, New York, 1973 in the article by Francis et al, "Chemical Agents in the Control of Calcification Processes in Biological Systems," pages 57–83, particularly at pages 75–78, an antinucleating agent (e.g., a diphosphonate) can in sufficient quantity at a physiological pH completely absorb onto a spherical nucleated particle of hydroxyapatite as it forms and entirely block crystal growth. In this way, the formation of large insoluble crystals of apatite is prevented and coated small hydroxyapatite crystals of higher water solubility are attained.

It has been found that not all antinucleating agents can successfully stabilize calcium ions and phosphate ions against precipitating to form large insoluble apatite crystals. For instance, such insoluble crystals form when it is sought to use antinucleating agents such as sodium hexametaphosphate, sodium pyrophosphate, sodium phytate and mellitic acid as well as disodium-phosphonoethane-1,2-dicarboxylate, 1,1-diphosphonopropane-2,3-dicarboxylic acid monohydrate, 3-amino-1-hydroxypropane-1,1-diphosphonic acid and imino diacetic-N-methylene phosphonic acid. On the other hand, the antinucleating agents of the present invention successfully stabilize the calcium ions and phosphate ions against precipitation as large insoluble apatite crystals at a pH between about 5 and 9. Preferably, the pH is about 6.8 to about 7.5, which approximates usual human physiological conditions and is optimum for effecting remineralization. Desirably, the antinucleating agent of the invention is present in amount of about 4 to 5000 ppm ($1.5 \times 10^{-5}$ M to $2 \times 10^{-2}$ M) of the composition, preferably about 5 to 1000 ppm ($1.9 \times 10^{-5}$ M to $1 \times 10^{-2}$ M), such as about 5–60 ppm ($1.9 \times 10^{-5}$ M to $1.8 \times 10^{-4}$ M).

Certain antinucleating agents such as ethylene diamine tetramethylene phosphonic acid have been disclosed as effective antinucleating agent additives to solutions containing sources of phosphate, calcium and fluoride ions in U.S. Pat. Nos. 4,177,258 and 4,183,915 each to Gaffar et ux. In the present invention precipitation from calcium and phosphate ions in solution is inhibited with reduced weight levels of the antinucleating additive.

The antinucleating additive, 2-phosphono-butane-tricarboxylic acid-1,2,4 (PBTA) and its water soluble salts has the formula:

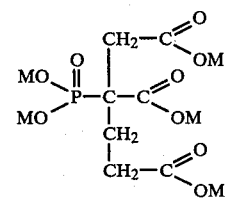

wherein M is independently hydrogen or an orally acceptable cation such as alkali metal (e.g. sodium or potassium), ammonium or $C_1$-$C_{18}$ mono-, di- or trisubstituted ammonium (e.g. mono-, di- or triethanolammonium) salt.

PBTA and its salts have been disclosed as dentifrice additive against staining due to a cationic agent in U.S. Pat. No. 4,224,309 and as an anticalculus additive in U.S. Pat. No. 4,224,308 as well as an inhibitor of corrosion of aluminum in U.S. Pat. No. 4,229,409 to Scharf et al. However, hitherto it was not known that it could be an effective inhibitor or precipitation of calcium and phosphate ions in a remineralizing solution.

The effective antinucleating agents render the remineralizing dentifrice stable at normally occurring temperatures, e.g., about 15° C.–40° C. The remineralizing agents can diffuse effectively through an intact enamel surface in order to act on subsurface lesions.

The stability provided by the effective antinucleating agents prevents spontaneous precipitation on enamel surfaces and thereby permits diffusion of the remineralizing components to subsurface lesions.

One or more sources of each calcium ions and phosphate ions may be employed. When the source is normally insoluble such as a calcium phosphate, it is solubilized during preparation of the solution, by maintaining an acid pH of about 6 or less (e.g., about 2.5 to 6) during preparation of the remineralizing solution, particularly before the effective antinucleating agent is added.

The normally insoluble sources of calcium and phosphate ions may be a single compound such as tricalcium phosphate (which substantially corresponds to hydroxyapatite, $Ca_5(PO_4)_3OH$ or $3Ca_3(PO_4)_2 \cdot Ca(OH)_2$, bone meal or dicalcium phosphate (dihydrate or anhydrous). When dissolved, particularly in the presence of fluoride ions, formation of hydroxyapatite, fluorohydroxyapatite and fluorapatite occurs.

Examples of other normally water-soluble or normally water-insoluble (but soluble at pH of about 6 or less) sources of calcium ion, but not phosphate ion, which can be used in the remineralizing dentifrice of the invention include calcium salts with acetate, gluconate, nitrate, stearate, lactate, formate, molybdate, tungstate, sulfate, alkyl sulfonate (e.g. lauryl sulfonate), oleate, tartrate, sorbate, iodate, silicate, aluminate, benzoate, citrate, fumarate, butyrate, isobutyrate, malate, maleate, propionate, valerate and the like. Mixtures of such calcium sources with each other or with calcium phosphate may be employed.

Examples of sources of phosphate ions, but not calcium ion, which can be used in the remineralizing dentifrice of the invention include the normally water-soluble or normally water-insoluble (but soluble at pH of about 6 or less) salts including alkali metal (e.g. sodium and potassium), ammonium, magnesium, barium and strontium orthophosphates and acid orthophosphates, metaphosphates, pyrophosphates, as well as glycerophosphates, fructose-6-phosphate, sorbitol-6-phosphate, glucose-1-phosphate, glucose-6-phosphate and the like. Mixtures of such phosphate sources with each other or with calcium phosphate may be employed.

Tricalcium phosphate or the other sources of calcium and phosphate which together form hydroxyapatite when dissolved are employed with the mole ratio of calcium ion to phosphate ion being from about 0,01 to about 100:1, typically about 0.2 to about 5:1, preferably about 1.2 to about 2:1, e.g., about 1.4 to about 1.7:1. A ratio of calcium to phosphate of 1.67:1 corresponds to the ratio of calcium to phosphate in dental enamel. The amount of calcium ion and phosphate ion in the dentifrice is sufficient to effect remineralization, there being typically at least about 500 ppm of each of calcium ion and phosphate ion. The maximum amount of calcium ion and phosphate ion desirable is that which would not result in precipitate formation. This could vary depending on the ion sources and the pH conditions. Typically, about 35,000 ppm of calcium ion and about 40,000 ppm of phosphate can be employed and precipitation still avoided.

In the prior art it has been difficult to maintain the solubility of calcium phosphate particularly in the presence of a fluoride source. As previously indicated, this is overcome in the present invention when the effective antinucleating agents are employed. Examples of fluoride ion sources (including complex fluoride ions) include alkali metal (e.g., sodium, potassium, lithium) ammonium, alkaline earth metal (e.g., calcium, barium, strontium, magnesium), aluminum, zinc, stannous, indium, zirconium, copper, nickel, palladium and organonitrogen such as alkylamine (e.g., hexylamine) compounds with fluoride ion sources. Sources of fluoride ions include fluoride, fluorophosphate (including monofluorophosphate, difluorophosphate and polyfluorophosphate), silicofluoride, fluorozirconate, fluoroborate and fluorostannite. Typical compounds are sodium fluoride, zinc fluoride, stannous fluoride and sodium monofluorophosphate. Sodium fluoride and sodium monofluorophosphate are preferred. The fluoride source compound is desirably present in amount to provide about 1 ppm to 10,000 ppm (0.0001%–1%) fluoride to the remineralizing dentifrice e.g., about 1 ppm to 1000 ppm (0.0001–0.76%) sodium monofluorophosphate, preferably about 5 ppm fluoride. The amount of the compound employed should not be sufficient to result in precipitate formation. For instance, in the case of a fluoride source of low solubility, such as calcium fluoride, the amount of the compound employed should not exceed 15000 ppm.

The stable remineralizing solution is prepared by adding the calcium ion and phosphate ion sources to water and lowering the pH to keep the solution clear. The ion sources may be a single material, such as tricalcium phosphate or may be a plurality of materials, such as calcium chloride and sodium dihydrogen orthophosphate. The ratio of calcium ion to phosphate ion may be from about 0.01 to about 100:1, but is desirably about 1.67:1 in order to optimally form hydroxyapatite, for instance using about 1.5 mM calcium ion and 0.9 mM phosphate ion in solution. A preservative such as sodium benzoate or methyl-4-hydroxybenzoate may be employed to reduce bacterial growth. An electrolyte salt as an alkali metal (e.g., sodium or potassium) chloride may be present (e.g., 1 to 1000 ppm) in the stable remineralizing solution to further improve stability and diffusion of remineralizing material into subsurface lesions.

Acidic materials are used to reduce the pH to about 2–4, typically about 2.8–3.8, in order to maintain clarity of the solution. Typical materials include phosphoric acid, hydrochloric acid and the like.

The pH is then raised to a mildly acid level, such as about 5 to 6.5, e.g. about 6, with baisc materials such as sodium hydroxide, potassium hydroxide, ammonium hydroxide and the like.

The solution can then be stabilized against precipitation by incorporating therein an effective antinucleating agent, such as 2-phosphono-butane-tricarboxylic acid-1,2,4 disodium salt. The antinucleating agent is added to the solution in amount of about $1 \times 10^{-6}$ M to $2 \times 10^{-4}$ M, typically about $1 \times 10^{-5}$ M (3 ppm) and thoroughly mixed therein.

The pH can then be maintained or even raised to about 9, with the effective antinucleating agent presenting precipitation of hydroxyapatite. Preferably it is raised to a physiological pH in the range of about 6.8–7.5, typically about 7 to 7.5. Basic materials of the type indicated may be employed to raise the pH.

A fluoride ion source such as sodium fluoride or sodium monofluorophosphate is then added in the indicated amount and the solution can be diluted to a desired concentration. In the solution of the present invention the fluoride does not cause the hydroxyapatite to precipitate.

Thus, the solution can be maintained for a long period of time, remaining effective when brought into contact with dental material to remineralize subsurface lesions. The solution can be used as such or incorporated into dental compositions, such as mouth rinse.

The solution of the invention may be applied to dental surfaces as such, for instance, by rinsing the mouth therewith or it may be incorporated into a mouthwash.

When incorporated into a mouthwash, the solution is typically about 20-80% by weight of the mouthwash, which mouthwash also includes a non-toxic lower aliphatic alcohol, such as ethanol, n-propanol or isopropanol. A surface active agent (e.g., about 1-5%) such as sodium lauryl sulfate, sodium N-lauroyl sarcosinate or polyoxyethylene-polyoxypropylene (Pluronic) material, a flavoring and/or sweetening material or antibacterial agent may also be present.

When incorporated into a dental cream or gel, the solution is typically about 20-60% by weight of the cream or gel.

The dentifrice typically contains about 10-50% of a dentally acceptable water-insoluble polishing material. Preferably the polishing material does not include calcium and phosphate moieties. Insoluble polishing materials containing calcium and phosphate moieties, such as dicalcium phosphate, would not provide calcium ions and phosphate ions in the amounts provided by the solubilized material in the dentifrice of the invention. Desirable polishing agents include hydrated alumina, silica (colloidal, precipitated or crystalline), dolomite, bentonite, melamine-formaldehyde resin, urea-formaldehyde resin and the like. Hydrated alumina and silica are preferred. The dental cream also generally contains humectant such as glycerine, sorbitol propylene glycol or polyethylene glycol 400 and gelling agent such as sodium carboxymethyl cellulose or Irish Moss. Also, surface active agent flavoring and/or sweetening material, antibacterial agent, antibacterial preservative, (e.g. sodium benzoate or methyl-4-hydroxy benzoate), silicone material, chlorophyll compound or ammoniated material may be present.

The following examples illustrate the invention but do not limit it. All parts, amounts and proportions are by weight unless otherwise noted.

EXAMPLE 1

A stock solution of hydroxyapatite (tricalcium phosphate) is prepared by adding hydroxyapatite to water to a final concentration of 1.5 mM calcium and 0.9 mM phosphate. Phosphoric acid is then added to 500 ml of the stock solution to produce a clear solution at pH 3.0 after which pH is raised to 5 with 1 N potassium hydroxide. Next PBTA is added and mixed in the solution to a concentration of 5 ppm. Sodium fluoride is then added to a concentration of 5 ppm. Following this additional potassium hydroxide is added to produce a pH of 7.0. Additional water is added to bring to 1 liter.

The solution thus formed remains stable and clear upon storage at 38° C. for 4 weeks. A similar solution without PBTA and without sodium fluoride results in precipitation by 10 seconds from the time of final pH rise. When sodium fluoride is present and PBTA is absent, precipitation occurs by 10 seconds from the time of final pH rise. Thus, a one part stable aqueous remineralization solution is obtained with an addition of a stabilizing agent.

Similar results are obtained using 10, 20, 25, 30, 40, 50 and 60 ppm of PBTA.

Similar results are also obtained using 5 ppm of sodium monofluorophosphate in place of sodium fluoride.

EXAMPLE 2

100 parts of the stock solution of Example 1 with sodium fluoride, calcium and phosphate is incorporated into 100 parts of the following mouthwash:

|  | PARTS |
|---|---|
| Ethanol | 6 |
| Pluronic F-10 8 (polyoxyethylene polyoxypropylene) | 2 |
| Glycerine | 15 |
| Benzoic acid | 0.01 |
| Sodium saccharin | 0.02 |
| Flavor | 0.075 |
| Sodium benzoate | 0.500 |
| Color | 0.0006 |
| Water | Q.S. to 100 |

The mouthwash remains stable upon storage and the calcium and phosphate ions remain dissolved therein.

EXAMPLE 3

The stock solution of Example 1 with sodium fluoride, calcium and phosphate is added in 1:1, 2:1 and 3:1 ratios to the following dental formulation:

|  | PARTS |
|---|---|
| Glycerine | 10.00 |
| Sorbitol (70%) | 17.00 |
| Water | 23.70 |
| Sodium Benzoate | 0.50 |
| Sodium Saccharin | 0.20 |
| Sodium Carboxymethyl Cellulose | 1.10 |
| Precipitated Silica | 45.00 |
| Sodium Lauryl Sulfate | 1.50 |
| Flavor | 1.00 |

It will be apparent to one skilled in the art that various modifications of the foregoing Examples may be made thereto.

We claim:

1. A stable aqueous remineralizing composition which comprises a solution of water having dissolved therein a source of calcium ions and a source of phosphate ions, the amount of calcium ion and phosphate ions being sufficient to effect remineralization of dental enamel; a compound which provides fluoride anticaries agent; and an antinucleating agent selected from the group consisting of 2-phosphono-butane-tricarboxylic acid-1,2,4 and water-soluble salt thereof, said solution having a pH of about 5-9.

2. The stable aqueous composition claimed in claim 1 wherein the pH of said solution is about 6.8 to about 7.5.

3. The stable aqueous composition claimed in claim 1 wherein said antinucleating agent is present in amount of about 4 to 5000 ppm.

4. The stable aqueous composition claimed in claim 3 wherein said antinucleating agent is present in amount of about 5-1000 ppm.

5. The stable aqueous composition claimed in claim 1 wherein an electrolyte salt is present.

6. The stable aqueous composition claimed in claim 1 wherein the mole ratio of calcium to phosphate is from about 0.01 to about 100:1 and at least about 50 ppm of each of calcium and phosphate is present.

7. The stable aqueous composition claimed in claim 6 wherein said source of calcium ions and of phosphate ions is hydroxyapatite and the mole ratio of calcium to phosphate is about 1.67 to 1.

8. The stable aqueous composition claimed in claim 1 wherein said source of calcium ions and of phosphate ions is dicalcium phosphate.

9. The stable aqueous composition claimed in claim 1 wherein said source of calcium ions is calcium chloride and said source of phosphate ions is sodium phosphate.

10. The stable aqueous composition claimed in claim 1 wherein said compound which provides fluoride anticaries agent provides about 1 ppm to about 1000 ppm.

11. The stable aqueous composition claimed in claim 10 wherein said compound which provides fluoride anticaries agent is sodium monofluorophosphate.

12. A mouthwash comprising a non-toxic lower aliphatic alcohol carrier and incorporated therein the stable aqueous remineralizing solution claimed in claim 1.

13. A mouthwash as claimed in claim 12 wherein said alcohol is ethanol and said solution is about 20–80% by weight of said mouthwash.

14. A dental cream or gel comprising water, a humectant, a gelling agent and a dentally acceptable polishing material and the stable aqueous composition claimed in claim 1.

15. The remineralizing dentifrice claimed in claim 14 wherein said dentifrice is a dental cream and comprises a dentally acceptable water-insoluble polishing material selected from the group consisting of hydrated alumina and silica.

16. The process of preparing a stable aqueous solution comprising incorporating into a stock solution containing calcium ions and phosphate ions at a pH of about 2–4 an antinucleating agent which prevents precipitation of said calcium ions and said phosphate ions selected from the group consisting of 2-phosphonobutane-tricarboxylic acid-1,2,4 and water-soluble salt thereof, adding to said stock solution a compound which provides fluoride anticaries agent and raising the pH to about 5–9.

* * * * *